US006563992B1

(12) United States Patent
Doyle

(10) Patent No.: US 6,563,992 B1
(45) Date of Patent: May 13, 2003

(54) SMALL DIAMETER DIFFUSE REFLECTANCE PROBE

(75) Inventor: Walter M. Doyle, Laguna Niguel, CA (US)

(73) Assignee: Axiom Analytical, Inc., Irvine, CA (US)

( * ) Notice: Subject to any disclaimer, the term of this patent is extended or adjusted under 35 U.S.C. 154(b) by 0 days.

(21) Appl. No.: 09/347,479

(22) Filed: Jul. 2, 1999

Related U.S. Application Data

(60) Provisional application No. 60/091,654, filed on Jul. 2, 1998.

(51) Int. Cl.[7] .............................. G02B 6/04; G01J 1/04
(52) U.S. Cl. ........................ 385/115; 385/12; 385/31; 250/227.11; 250/227.14
(58) Field of Search .............................. 385/12, 31, 38, 385/115, 116; 250/227.11, 227.14, 227.18

(56) References Cited

U.S. PATENT DOCUMENTS

| 5,625,459 A | * | 4/1997 | Driver | 250/227.24 |
| 5,754,722 A | * | 5/1998 | Melling | 250/576 |
| 5,818,996 A | * | 10/1998 | Doyle | 385/115 |
| 5,974,210 A | * | 10/1999 | Alcock et al. | 250/227.18 |

* cited by examiner

Primary Examiner—Brian Healy

(74) Attorney, Agent, or Firm—Myers Dawes & Andras; Joseph C. Andras

(57) ABSTRACT

The invention relates to a fiber-optic coupled diffuse reflectance probe that is adapted to detachably connect to a bifurcated fiber bundle. The probe includes a solid light guide for separating the bundle from the target within a small-diameter probe body. A probe of this construction is especially useful for analyzing high temperature and high pressure targets, through relatively small fittings, as is required in polymer extrusion applications. The solid light guide may extend along all or along a lesser portion of the probe body's length. Its fiber-end may be coupled directly to the illumination and detector fibers or indirectly, and at some distance from the fibers, by way of a lens or a hollow light guide. Its target-end may be exposed to terminate in a direct face-to-face relationship with the target, or it may be located behind an intermediate window. The solid light guide is characterized by a target-end refracting surface that minimizes stray light. In particular, such surface is designed to ensure that light internally reflected from that surface with bounce back to the detector fiber at angles that are outside of the detector fiber's field of view. The preferred surface is a beveled plane, but other flat and nonflat surfaces are possible. The target-end refracting surface also tends to ensure that reflections from the window surfaces, if present, are returned to the detector fiber at angles outside of its field of view. The window itself may be canted too to help ensure that rays which are unusually divergent due to imperfections are still returned to the the detector fiber at angles outside of its field of view.

18 Claims, 7 Drawing Sheets

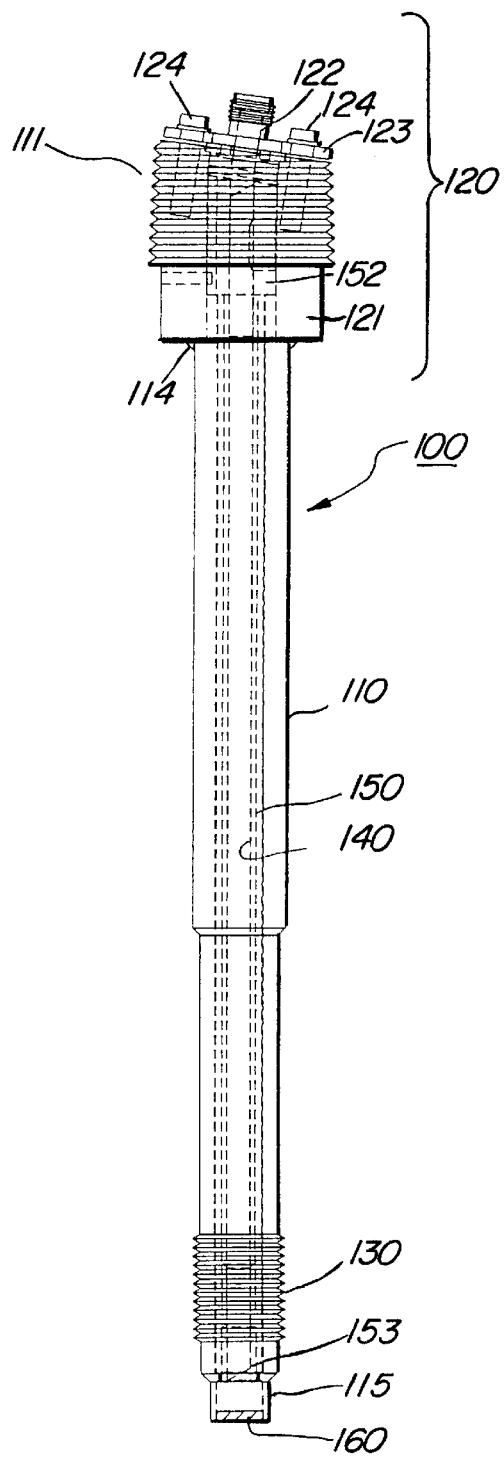
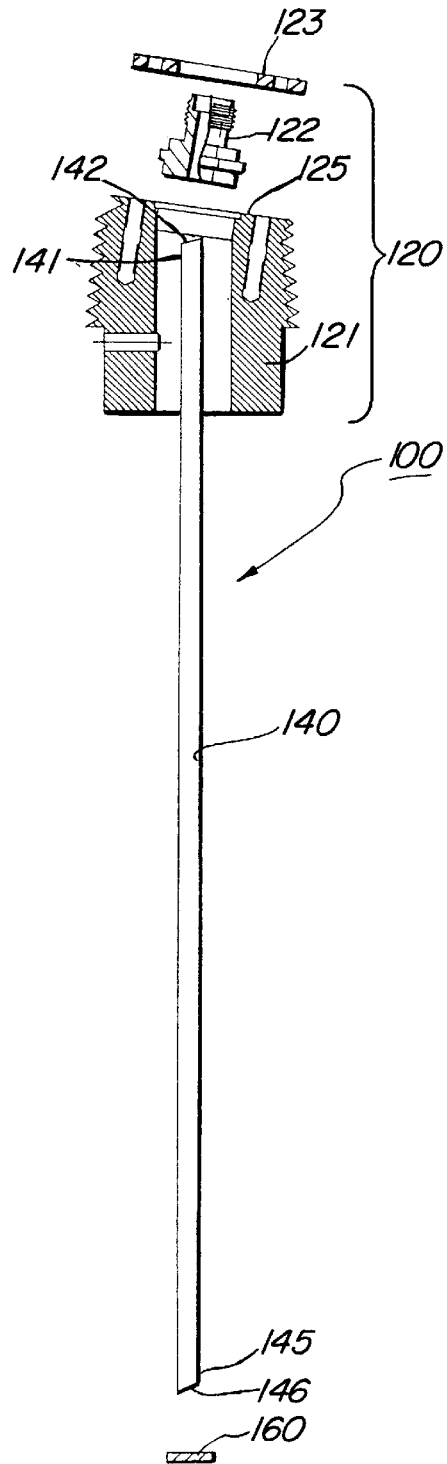

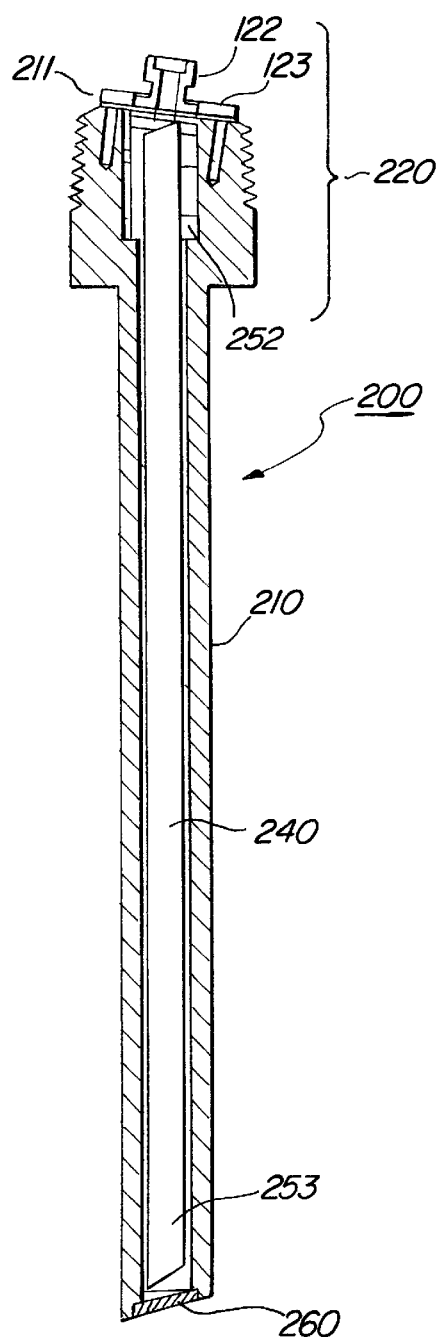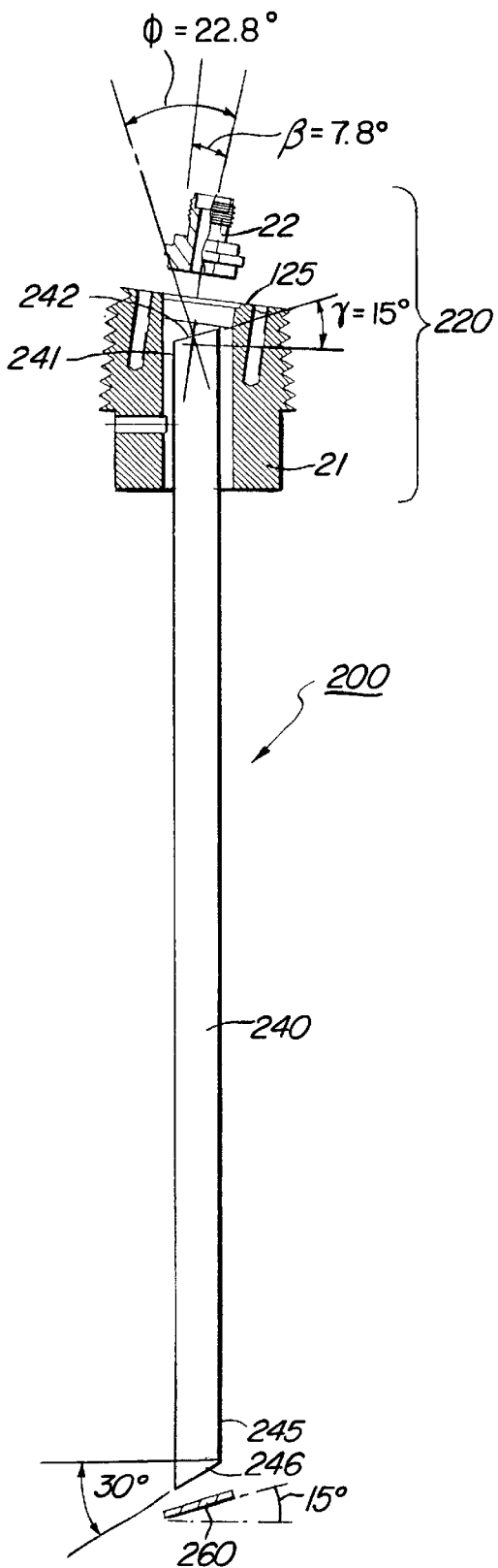

SMALL DIAMETER DIFFUSE REFLECTANCE PROBE

This application claims the benefit of U.S. Provisional Application No. 60/091,654, filed Jul. 2, 1998.

BACKGROUND OF THE INVENTION

1. Field of the Present Invention

The present invention relates generally to diffuse reflectance spectrometry and, more particularly, to diffuse reflectance probes of the type that uses a fiber-optic bundle for transmitting radiation to and then gathering radiation reflected from a diffusely reflecting substance.

2. Description of the Related Art

Diffuse reflectance spectroscopy ("DRS") has been used for many years to analyze a wide variety of materials. The sample interfacing techniques used have fallen into three broad categories depending on whether the optical spectrum used is in the visible region, the mid infrared region, or the near infrared region.

In the visible region of the spectrum, DRS devices have historically used the integrating sphere technique. Integrating spheres are attractive because they can collect virtually all of the radiation reflected from a surface, independent of direction. They are quite practical in the visible region due to the availability of large area highly sensitive optical detectors and extremely reflective diffuse white coatings for use on the inside of the spheres.

In the mid infrared region ("mid-IR") of the spectrum (fingerprint), integrating spheres have found only occasional use because the reasonably fast mid-IR detectors that are available are relatively small and insensitive and because the diffusely reflective coatings that are available for use in this region do not have the desired reflectance. Instead, most mid-IR DRS sampling systems have used specularly reflecting optical elements such as cassagrains, off-axis paraboloids, or ellipsoids to image the illuminated target directly on a small detector with a minimum number of reflections.

In the near infrared (NIR) region, the history of DRS is quite distinct from both visible and mid-IR DRS. NIR region devices have, in fact, followed a completely different development path. NIR instruments were first developed in the 1970's to inspect grains and other agricultural products. The operation of these early NIR devices was based on switching between relatively small number of fixed frequency optical filters so as to acquire what amounts to a very low resolution spectrum. As a result of the low resolution, the response speed required of the IR detectors was quite modest, allowing large detectors to be used. A-typical NIR grain analyzer would thus have a modulated beam of radiation illuminating a small cup of ground up grain. The region above the cup would be occupied by hemispherical array of large area detectors all hooked together so as to collect the maximum possible amount of scattered radiation. This approach is somewhat similar to the methods used to study visible diffuse reflectance except that an array of detectors is used rather than a single detector and an integrating sphere.

Since the development of these early instruments, NIR systems have become more sophisticated, with dispersive spectrometers arriving first, followed by fourier transform infrared ("FTIR") spectrometers being applied in the NIR region of the spectrum.

NIR is used in many fields due to the availability of near-IR transmitting fiber optics for coupling a spectrometer to a remote measurement location. However, sampling optics for use with these newer systems have tended to develop out of the "brute force" tradition started with the earlier NIR region grain analyzers. The most common approach to diffuse reflectance analysis in the NIR region uses a large bundle of fibers that may be one inch (1") in diameter, or more. In some cases, a few of the fibers are used to illuminate the sample with spectrally modulated radiation while the rest of the fibers are used to collect the radiation scattered over a wide range of angles, the collected radiation being conveyed to a single large detector or an array of detectors. Others have conversely illuminated the sample with a large bundle of fibers which obtain their radiation from a large IR source and then used a smaller bundle or even a single fiber to collect a sample of the reflected radiation and route it to the spectral modulator and a small area detector.

The use of a large fiber bundle has a number of drawbacks. Among these are the high cost of large fiber bundles for use at wavelengths much longer than 1 $\mu$m, the limited areas of fast response detectors for use at longer wavelengths, and the fact the throughput of FTIR spectrometers does not allow the use of large bundles. The latter drawback is especially unfortunate because FTIR instruments are becoming increasingly popular for use in the NIR region due to their high frequency stability.

Even when small bundles or single fibers are used for both sample illumination and reception, most workers in the field have continued to use brute force, simply pointing the fibers at the sample. The most successful device of this nature, as shown in FIG. 1a and 1b, uses a bifurcated fiber bundle 90 and terminates that bundle directly next to the target 50 without any other optics. The bifurcated fiber-bundle 90 has a number of individual transmitting or illumination fibers 91 and a number of individual receiving or detector fibers, 91, 92 (eg. eighty fibers total) that are randomly distributed within a tip bundle 95 that splits into two smaller leg bundles (eg. forty fibers each) 93, 94. One leg bundle 93 carries radiation from a radiation source 70 to the target 50 while the other leg bundle 94 carries radiation reflected from the target to a detector 80.

In an earlier patent application (Ser. No. 08/784,823), I disclose a diffuse reflectance probe featuring low stray light, detachability from a fiber-optic bundle, and the ability to analyze samples either in contact with the probe or displaced from it. Since filing that application, I have become familiar with a need for diffuse reflectance probes suitable for the analysis of molten polymers at high temperatures and pressures and have developed a new probes for such use based on some of the principles disclosed in my earlier application. However, it has also become apparent that the applicability of diffuse reflectance to hot polymer melt analysis would be much more useful if such a probe could be provided in a structure compatible with certain types of fittings available on many polymer extruders. The external threads that engage two such fittings are specified as or "½–20 N.F. THD" and "M18×1.5 THD", being only about ½" and ⅝" in diameter, respectively. These fittings mandate a very limited diameter in which to house the probe optics. While it is possible that the earlier design could be adapted to such a small diameter situation, it is likely that this would result in a significant reduction in usable signal level. I have thus developed a new and innovative design which is more inherently compatible with the small available diameter.

SUMMARY OF INVENTION

The invention may be regarded as a diffuse reflectance probe for connection to a illumination fiber for carrying radiation from a remote source and illuminating a target and for connection to a return fiber for carrying target-modified radiation that is diffusely reflected from the target back to a remote detector for diffuse reflectance analysis, the diffuse reflectance probe comprising: a solid light guide having a fiber end with a fiber-side refractive surface, a target end with a target-side refractive surface, and an optical axis extending between the fiber end and the target end; and a fiber coupling structure optically interfacing the fiber-side refractive surface to the illumination fiber and to the detector fiber; the target-side refractive surface being oriented relative to the normal of the optical axis to minimize stray radiation that comes from the remote fiber and does not reach the target, but rather is reflected back toward the detector fiber via the solid light guide and the fiber coupling structure, from entering the detector fiber and overpowering the target-modified radiation.

In a more specific embodiment, the invention may be regarded as further including a window interposed between the target-side refractive surface and the target, wherein the window has first and second refractive window surfaces that potentially contribute to stray radiation by reflecting some radiation from the illumination fiber back toward the detector fiber via the solid light guide and the fiber coupling structure; and wherein the acute angle of the target-side refractive surface at the target end of the solid light guide is oriented relative to the normal of the optical axis and to the first and second refractive window surfaces as to also cause substantially all radiation that is reflected from the first and second refractive window surfaces to reach the detector fiber at angles that are outside the detector fiber's half angle of acceptance.

In an even more specific embodiment, the window in the diffuse reflectance probe has its first and second window surfaces are oriented at an acute angle relative to the normal of the optical axis to further ensure that illumination rays within the light guide that are directed outside of the angle of divergence that is mathematically expected, due to imperfections and the like, are still reflected from the first and second window surfaces at an angle that cause such rays to refracted through the second refractive surface at the target end of the light guide at an angle that is outside the detector fiber's half angle of acceptance.

BRIEF DESCRIPTION OF THE DRAWINGS

FIG. 2 is an elevational view of a first preferred embodiment of a diffuse reflectance probe according to this invention that uses a ⅛" diameter solid light guide;

FIG. 3 is a simplified view of the probe shown in FIG. 2 (with the probe body, light guide sleeve, and other parts eliminated) that more clearly shows the ⅛" diameter solid light guide and orthogonal window that are characteristic of this embodiment;

FIG. 5 is an elevational view of a second preferred embodiment of a diffuse reflectance probe according to this invention that uses a ¼" diameter solid light guide;

FIG. 6 is a simplified view of the second preferred probe of FIG. 5 (with the probe body and other parts eliminated) that more clearly shows the ¼" diameter solid light guide and a canted window that are characteristic of this embodiment;

FIGS. 13 to 17 are schematic representations of various light lengths and various target-end configurations that are encompassed by this invention, wherein:

FIG. 13 represents an alternative embodiment wherein the solid light guide is sufficiently long as to occupy substantially all of the probe body (not shown), that has a target-side surface that is a flat bevel, and that is exposed to the target at the end of the probe body;

FIG. 14 represents an alternative embodiment wherein the solid light guide has either a rooftop or a cone shape that is either steep (as shown) or shallow (not shown) so as to not form a retroreflector with an included angle of 90 degrees;

FIG. 15 represents an alternative embodiment wherein the solid light guide is relatively short and is interfaced to the fibers through a hollow light pipe;

FIG. 16 represents an alternative embodiment wherein the sold light guide is located behind an orthogonal window; and FIG. 17 represents an alternative embodiment wherein the sold light guide is located behind a canted window.

DETAILED DESCRIPTION OF THE PREFERRED EMBODIMENT

Figure 1A:
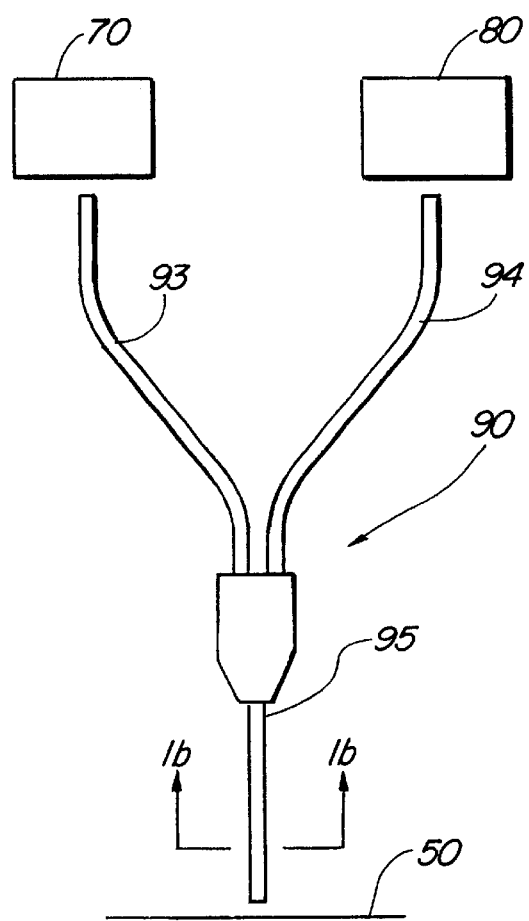
FIG. 1a shows a conventional bifurcated fiber-bundle 90 having a tip bundle 95 that splits into separate leg bundles 93, 94.

The invention disclosed herein relates to a diffuse reflectance probe having a solid light guide structure. It should be noted at the outset that the term "probe" is used to generally describe a sampling device. It does not require that the sampling device be elongated or be contained in a hand held structure. The inventor uses the term in a more general fashion. A probe according to the present invention could be hand held, flush mounted in a table below passing articles, mounted "cross-line" fashion in a flow conduit to observe passing material, or in any possible manner suitable for measuring a target.

The novel structure disclosed and claimed herein is especially suitable for high temperature, high pressure application because it confines the analytic radiation to a small diameter and keeps the overall probe relatively thin (a practical requirement for physical connection in certain applications), enables a more "robust" probe by subjecting only a small area to any high pressure that may be present, and keeps the relatively fragile fibers a safe distance away from the hot material being analyzed.

This invention, therefore, provides a diffuse reflectance probe having the following combination of characteristics: high collection efficiency, negligible stray light, small diameter, provision for removal from the associated fiber-optic cable, capability of operating at high temperature, and provision of a sample contacting window capable of withstanding high pressures.

A. The Mechanics

FIG. 2 is a side view of a first preferred diffuse reflectance probe 100 according to this invention. As shown, the probe 100 includes a probe body 110 that has a fiber end 111 and a target end 115 and further includes a solid light guide 140 that is housed inside of the probe body 110 behind a window 160. The window 160, made of sapphire or comparable material, may be brazed against a recessed shoulder in the tip of the probe body 110, but other more pressure-resistant structures and methods of attachment may be used. The difference between a light guide 140 and a window 160 in the context of this invention is that most rays bounce at least once within the former and most rays are merely refracted through the latter.

The solid light guide 140 of this first embodiment is relatively thin and fragile, having a diameter of only ⅛". Under such circumstance, the light guide 140 may be further secured within a sleeve assembly 150 that fits concentrically within the probe body 110. The sleeve assembly, as shown most clearly in FIG. 4, has a central tube 151 extending between a first retainer 151 and a second retainer 152 that engage the interior of the probe body 110 at its fiber end 111 and target end 115, respectively.

The solid light guide 140 itself has a fiber-end 141 with a fiber-side refractive surface 142, a target end 145 with a target-side refractive surface 146, and an optical axis (not explicitly shown) extending between these two ends. The preferred solid light guide 140 is made of fused silica, but other optical materials that form an inernally-reflective, solid light pipe may be used to suit a particular application and band of radiation.

Figure 1B:
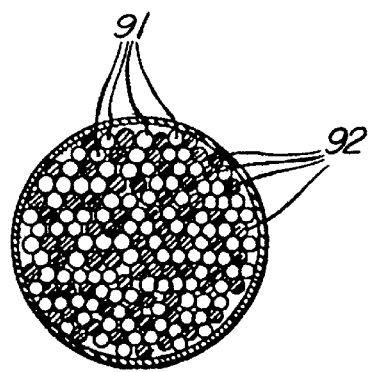
FIG. 1b is a cross sectional view of FIG. 1a, taken along section lines 1b—1b, showing the random distribution of the transmitting and collecting fibers 91, 92 within the tip bundle 95.

The probe 100 further comprises a fiber coupling structure 120 for optically interfacing the fiber-side refractive surface 142 to the illumination fibers 91 and detector fibers 92 exposed at the end of a fiber bundle 90 (not shown, but see FIGS. 1a and 1b). The fiber coupling structure 120 may be an extension of the probe body 110 as shown, or it may be an integral part of the probe body 110. In this particular case, the fiber coupling structure 120 consists of a main body 121 that is suitably secured to the probe body 110 (e.g. with a weldment 114 as shown) and a fiber connector for receiving the fiber bundle (e.g. a standard SMA connector 122 that is secured to the main body 121 by a connector clamp 123 and a pair of screws 124). The fiber connector 122 may be secured to the main body 121 so as to hold the fibers in alighment with the optical axis of the light guide 140. However, the main body 121 preferably has a canted mounting surface 125 that holds the fiber connector 122 at an angle and cause it, in turn, to hole the fibers with their axes at an angle relative to the elongated axis of the light guide 140 and probe body 110. The reasons for this will be discussed more extensively in the optical section below.

As first mentioned above in the background section, the probe 100 may further include a suitable connector 130 at its target-side end for connection to other equipment so that the probe 100 may operate in a "cross-line" fashion. The particular connection shown includes a threaded section 130 that engages a standard fitting that may be provided, for example, perpendicular and open to the flow channel of an extruder (not shown).

FIG. 3 is a simplified view of the probe shown in FIG. 2. In particular, this figure shows the probe 110 without the probe body 110, sleeve assembly 150, and screws 124 to more clearly show the relationship between the solid light guide 140 and orthogonal window 160 that are characteristic of this embodiment.

Figure 4:
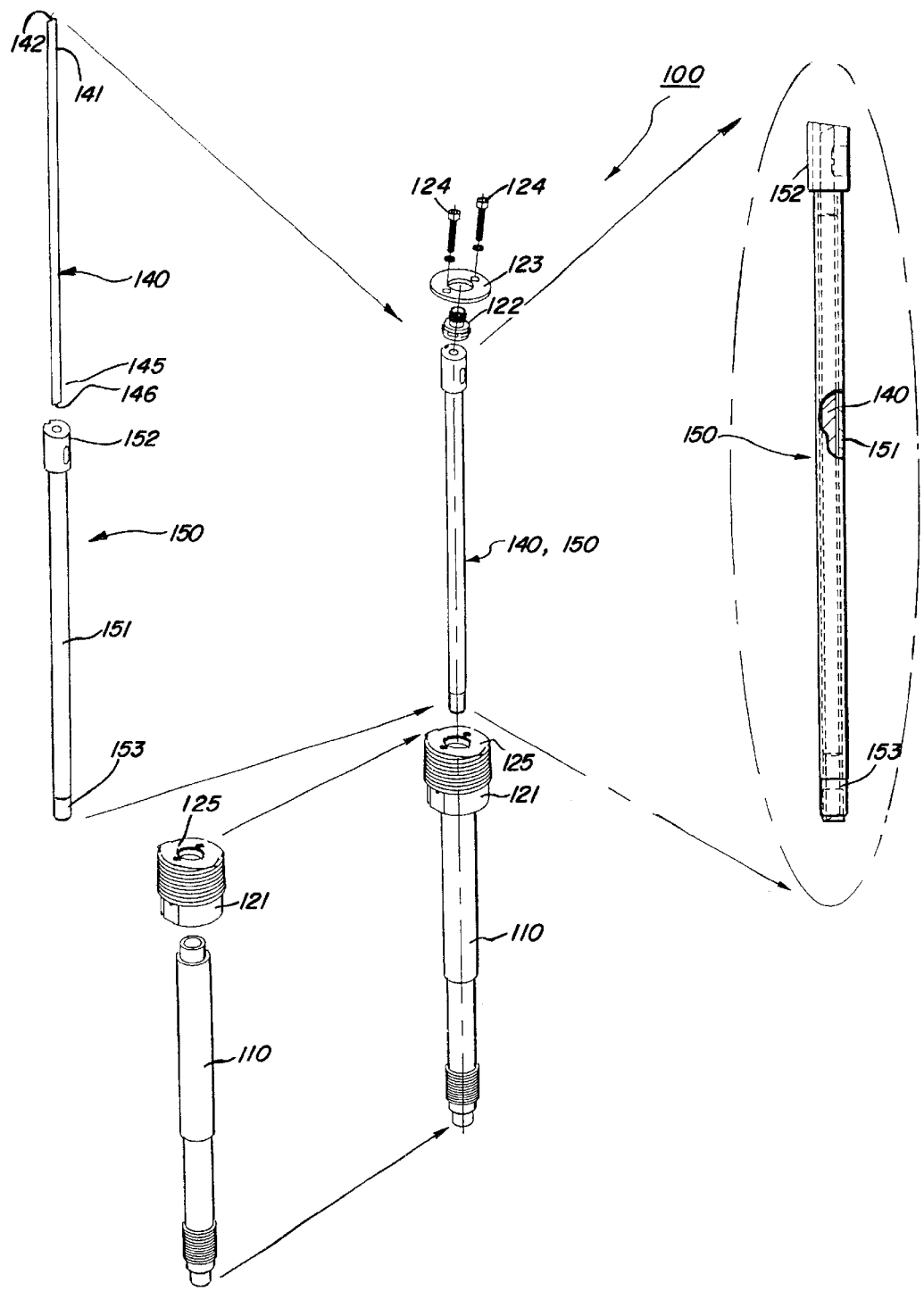
FIG. 4 is a multiple direction, exploded view of the probe shown in FIG. 2.

FIG. 4 is a multiple component, exploded view of the probe 100 shown in FIGS. 2 and 3. Here, as emphasized by the inwardly converging arrows, one can see the manner of assembling the main body 121 of the fiber coupling structure to the probe body 110, of assembling the solid light guide 140 into the sleeve assembly 150, of then inserting the sleeved light guide 140, 150 into the probe body 110, and of finally mounting the fiber connector 122 to the main body 121 with the connector clamp 123. The structure of the sleeved light guide 140, 150 may be best understood by following the diverging arrows from the center of FIG. 4 out to the partial cut-away view of that assembly in the insert surrounded by a dashed oval.

FIG. 5 is an elevational view of a second preferred diffuse reflectance probe 200. This embodiment is similar to the embodiment of FIGS. 2 to 4 so identical parts are identified with identical numbers (e.g. 121 and 121) and similar parts are identified by similar numbers having the same suffix (e.g. 140 or 240, 152 or 252, and so on). There are two especially notable distinctions between the second probe 200 and the first probe 100. The second probe 200 uses a canted window 260 (rather than an orthogonal window 160) and a larger light guide 240 (¼" dia. as opposed to ⅛" dia.) that in turn drives certain other differences.

FIG. 6 is to FIG. 5 as FIG. 3 is to FIG. 2. In particular, FIG. 6 is a simplified view of the second preferred probe 200 of FIG. 5 (with the probe body 210 and other parts eliminated) that more clearly shows the ¼" diameter solid light guide 240 and the canted window 260 that are characteristic of this embodiment;

As explained more carefully below with reference to the optical diagrams, the canted window 260 helps further reduce stray light beyond that offered by the solid light guide's canted target-side refractive surface 246. In particular, the canted window 260 makes it more likely that a ray has been scattered or deflected due to manufacturing imperfections and the like and thereby leaves the light guide 240 at an unexpectedly divergent angle, is then partially reflected back into the light guide 240 by the first or second refractive window surfaces reflections, and ultimately reaches the fiber bundle 90 at an angle that is outside the field of acceptance of a detector fiber 92. The canted window 260 is preferred, therefore, unless the cant will interfere in some way with the physical process that is being monitored.

The larger light guide 240 offers a larger area over which to average the radiation that reflected from a granular material (e.g. polyethylene pellets). On the other hand, the larger light guide 240 requires a larger overall probe. The best choice between physical size and averaging capability is subject to determination on an application by application basis. From this point of view, therefore, the first and second probes 100, 200 are equally preferred.

One final distinction between the first and second probes 100, 200 relates to the different diameter light guides 140, 240. In the second probe 200, the ¼41 light guide 240 occupies most of the interior of the probe body 250. Accordingly, the retainers 252, 253 must be secured directly to the light guide 240 (by applying epoxy to both the retainer and to the guide via a side hole for example), rather than to a central tube that receives the light guide as with the first probe 100. All other things being equal, the light guide 140 is preferably held in the sleeve assembly 150 so that it is not subject to contact from an adhesive which may impart some optical imperfections to the guide.

It should be understood that the first and second probes 100, 200 are preferred embodiments, there being many other variations that would come within the scope of this invention. In particular, as discussed further below, many different fiber coupling structures may be used to interface the illumination fiber and detector fiber to the light guide's fiber-side refracting surface. Moreover, the solid light guide may extend for substantially the full length of the probe body and be coupled "directly" to the fibers within a relatively confined region, or extend for only part of its length and be coupled to the fibers with a hollow, internally reflective light guide. The solid light guide may be located behind an NIR transparent, pressure-resistant window that is orthogonal or canted (preferred) at a suitable angle. The window need not be present at all, however, because the solid light guide itself may double as the window. Finally, the preferred target-side refractive surface is a bevelled, flat surface, but it may have any other suitable flat or non-flat geometry that provide the desired result.

B. The Optics

In approaching a unique optical design that enables a small diameter probe like those shown above, I first decided to eliminate the use of lenses in the small diameter portion of the probe and to keep optical radiation as nearly collimated as practical in this part of the probe. This could be done by simple running a bifurcated fiber-optic bundle down through the probe to a point where it is nearly in contact with the sample as shown in FIG. 1a. This approach provides nearly optimum signal level as long as the distance from the bundle to the sample is large compared to the separation between transmitting and receiving fibers and small compared to the overall fiber bundle diameter. However, there are three major objections to this simple approach. First, for most applications, it is necessary to place a window between the bundle and the sample. For high pressure applications, the window must be relatively thick. As a result, even if the bundle is placed quite close to the window, the distance from the bundle to the second window surface will be such that reflection from this surface will be a significant source of stray light. Second, it is often essential to terminate the fiber bundle at some distance from the probe window so that it will not be subjected to high temperatures. Third, it is very desirable to be able to detach the bundle from the probe—as was discussed in my earlier application.

There are two essential elements to my invention. The first is the use of a solid light guide to efficiently couple the optical radiation between the fiber bundle at the rear of the probe and the target beyond the tip of the probe via an unusually thin probe body. The light guide beneficially confines the bundle of radiation to a fixed diameter while maintaining its angular divergence. The second element is the key element of the invention in that it enables the first. This is the provision of at least one refractive surface adjacent to the target-end of the light guide at such an angle as to refract the radiation into a range of angles for which light reflected from this surface or from subsequent window surfaces (if any) will not be collected by the receiving fibers. In the preferred embodiments of the invention, a window is present and the light guide is a solid refractive element having a target-side refractive surface that is angled adjacent to to the window. Specific embodiments of the invention are discussed below.

Figure 7:
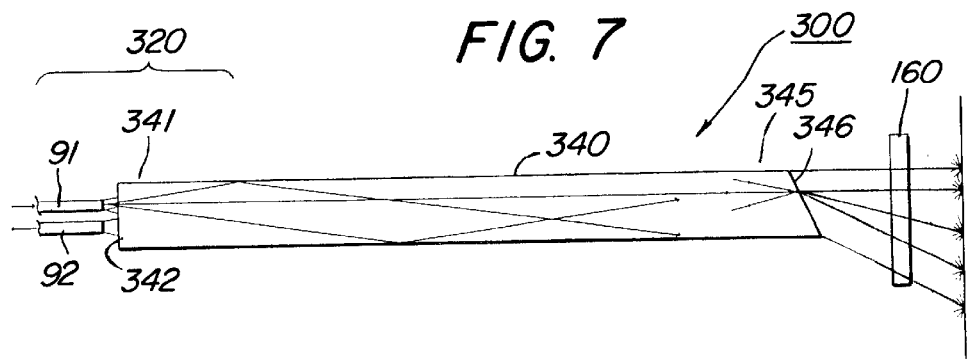
FIG. 7 is a schematic view of a third embodiment that has a target-end that is similar to that in the probe of FIG. 2, but has a "straight-on" fiber coupling structure at the fiber end of the solid light guide.

FIG. 7 is an optical diagram of a relatively generic embodiment that is well suited to presenting the optical features of the overall invention. This embodiment has a solid light guide 340 that is similar to the light guides 140, 240 first discussed above in that it too has a canted target-side refractive surface 346 at its target end 345. The fiber-side 341, though, is different. In particular, in FIGS. 2 to 6 discussed above, the SMA connector 122 and associated fiber-side refractive surfaces 142, 242 are canted relative to a plane that is normal to the optical axis. In FIG. 7, however, the solid light guide 340 has a fiber end 341 with a fiber-side refractive surface 342 that is precisely orthogonal to the optical axis of the light guide 340.

At the left side of this figure, a pair of optical fibers 91, 92 are "close coupled" to the flat fiber-side refractive surface 342 of the solid refractive light guide 340, one fiber 91 being used to couple radiation into the light guide 340 and the other 92 to collect a portion of the radiation traveling back through the light guide 340 and transmit it to an optical receiver (see e.g. 80 in FIG. 1a). Two fibers is the most general case. In all likelihood, however, more than two fibers would be used. One example would use a bifurcated bundle of fibers 90 as shown in FIG. 1b, where some of the fibers 91 are used for transmission to the light guide 340 and the rest 92 are used for collecting radiation from the light guide 340.

Figure 8:
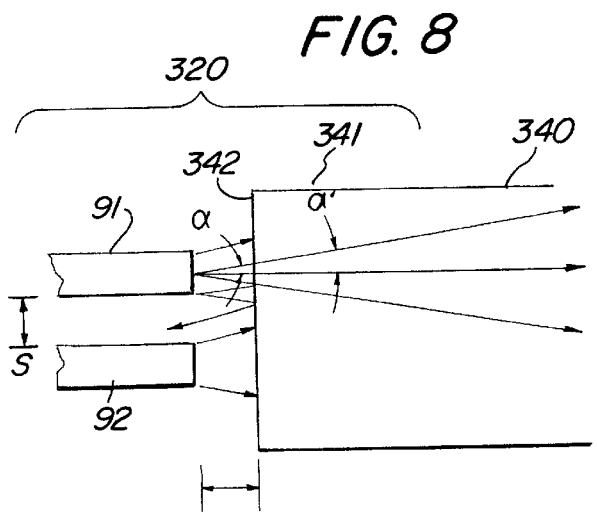
FIG. 8 is a close-up schematic view of the target-end of a solid light guide having a canted target-side surface that is located behind an orthogonal window as in the first embodiment of FIG. 2 to 4.

FIG. 8 is an enlargement of a portion of FIG. 7 showing the coupling between the fibers 91, 92 and the light guide 340. The maximum angle of divergence of radiation traveling through each illumination fiber 91 is determined by the numerical aperture (NA) of the fiber, i.e.:

$$\alpha = \sin^{-1}(NA). \tag{1}$$

On entering the light guide 340, this divergence angle is reduced to the following value:

$$\alpha' = (1/n)\sin^{-1}(NA), \tag{2}$$

where "n" is the refractive index of the light guide.

In order to eliminate stray light arising from reflection at the input surface of the light guide 340 in this straight-on arrangement, the separation "p" between the optical fibers 91, 92 and the light guide 340 must be no greater than $$p = s/2 \tan \alpha, \tag{3}$$

where "s" is the separation between the cores of the transmitting and receiving fibers 91, 92.

The embodiment just described has one distinct drawback. In order to eliminate stray light contributions from the first fiber-side surface 342 of the light guide 340, we have had to place the transmitting and receiving fibers 91, 92 very close to this surface. For example, using Equation (3), above we find that if the minimum distance between the core of a transmitting fiber 91 and that of a receiving fiber 92 is 0.02 mm, the separation between the fibers and the light guide must be less than 0.044 mm. At separations this short, we are likely to experience interference fringes between the opposing refractive surfaces at the outputs of the fibers 91,92. These fringes can lead to unpredictable frequency dependent changes in signal level and can thus degrade measurement accuracy.

Figure 9:
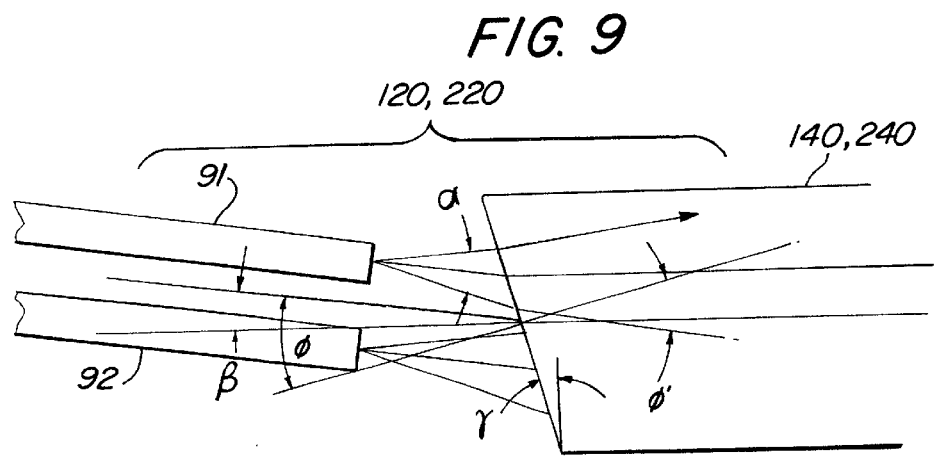
FIG. 9 is a close-up schematic view of the target-end of a solid light guide having a canted target-side surface that is located behind an canted window as in the second embodiment of FIGS. 5 and 6.

The solution to the problem just stated is shown in FIG. 9, which figure shows a preferred fiber coupling structure 120, 220 of my invention. In this embodiment, the fiber-side end surface 142, 242 of the light guide 140, 240 is set at an angle of $\gamma$ relative to the normal to the light guide axis. In addition, the axis of the fibers 91, 92 is set at an angle of $\beta$ relative to the light guide axis and the fibers are positioned so that their centerline intersects the center of the light guide's fiber-side end surface 142, 242. The angle of incidence of a ray parallel to the axis of the fibers 91, 92 is thus given by $$\phi = \beta + \gamma \tag{5}$$

There are two important keys to this embodiment of the fiber coupling structure 120, 220. First, both $\beta$ and $\gamma$ must be chosen so that no rays reflected from the fiber-side end surface 142, 242 fall within the field of view of the receiving fibers 92. Second, these angles must be chosen so that the axis of the transmitted radiation, after refraction at the fiber-side end surface 142, 242, is parallel to the optical axis of the light guide 140, 240. This is especially important since any departure from parallelism of the two axes will lead to an increase in the overall divergence of the beam after reflection of various rays from the walls of the light guide 140, 240. This requirement is equivalent to setting $\gamma = \phi'$.

The requirement that no reflected rays fall within the field of view of the receiving fiber 92 equivalent to setting $\phi > \alpha$ where, again, $\alpha$ is the half angle field of view of the fibers, and $\phi$ and $\phi'$ are related by Snell's law:

$$\sin \phi = n \sin \phi'.$$

Thus, for example, if we use n=1.5 and set $\phi' = \gamma = 15$ deg., we have $\phi = 22.8$ deg., which is well beyond the typical acceptance angle of a fiber 92 (some common fibers have an NA of 0.22, corresponding to an acceptance angle of 12.7 deg.). In addition, we obtain $\beta = 7.9$ deg. These angles of $\gamma = 15$ deg., $\phi = 22.8$ deg., and $\beta = 7.9$ deg are shown in context at the top of FIG. 6.

Figure 10:
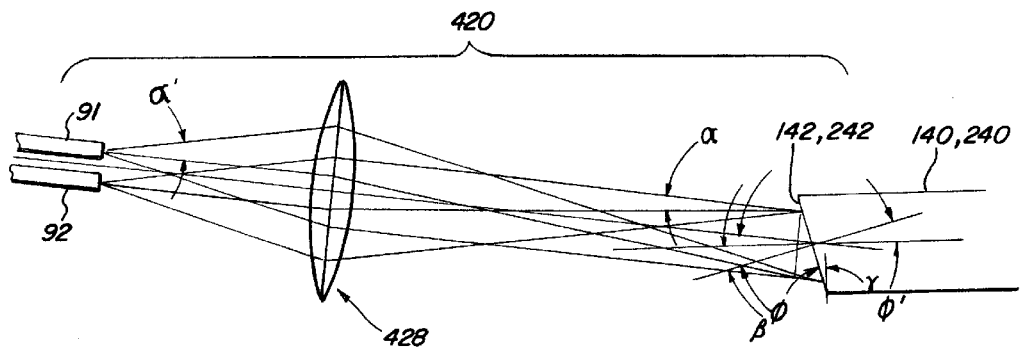
FIG. 10 is a close-up schematic view of a first exemplary fiber coupling structure wherein the axes of the fibers are aligned with the axis of the solid light guide.

FIG. 10 shows a third fiber coupling structure 420 that may be used in my invention. In this embodiment, an optical system 428 (here shown as a single lens) is used to image the end of the fibers 92, 92 (or fiber bundle 90) on the entrance aperture corresponding to the fiber-side end surface 142, 242 of the light guide 140, 240. This provides optimum coupling in cases where the diameter of the fiber-optic bundle (not shown) is different from that of the light guide 140, 240. If the bundle diameter is less than that of the light guide 140, 240, this fiber coupling structure 420 advantageously conserves the throughput of the overall system while reducing the divergence angle both within the light guide 140, 240 and in the air regions (not separately numbered) at either end of the light guide 140, 240. This, in turn, reduces the required angles of tilt at both the fiber-side end surfaces 142, 242 and target-side end surfaces 146, 246, respectively, leading in turn to a reduction in the amount of deflection of the output beam. This reduced deflection allows a closer match between the diameter of the light guide 140, 240 and that of the window (if present) without sacrificing efficiency. Since reflections from the lens 428 will contribute to stray light, practical probes based on this embodiment would, in most cases, include an optical stop blocking the middle of the lens, as taught in my earlier application.

Figure 11:
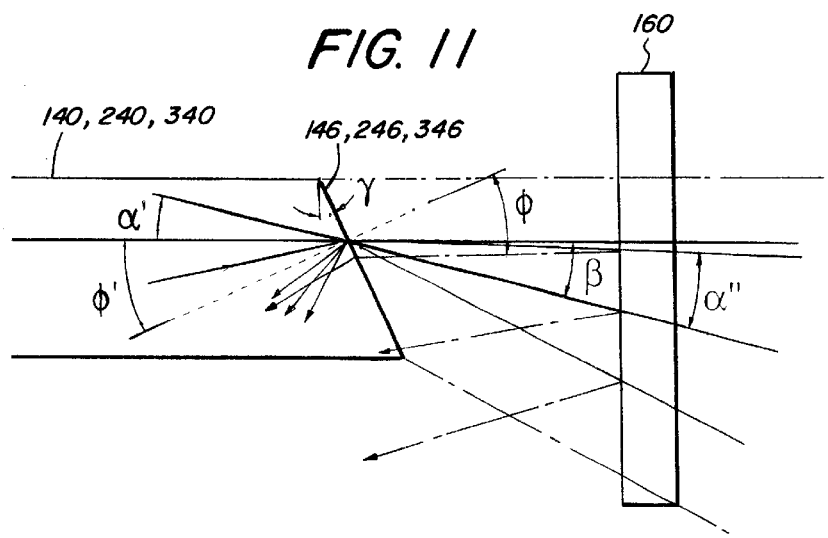
FIG. 11 is a close-up schematic view of a second exemplary fiber coupling structure wherein the axes of the fibers are canted relative to the axis of the solid light guide.

We now turn to FIG. 11 and carefully discuss what happens at the light travels to and ultimately exits the target-side end surface 146, 246, 346 of the light guides 140, 240, 340 as shown, for example, in FIG. 7. In this illustration, the various angles represented by the Greek symbols are not necessarily equal to the angles represented by the same symbols in FIG. 9.

If the light guide 340 is sufficiently long and narrow, most of the light rays traveling through it will be totally reflected at least once from its surface so that, at the far target-side end 345, the radiation will more or less uniformly fill the diameter of the light guide 340 with such radiation having a maximum divergence angle equal to $\alpha'$. If the far target-side end 345 of the light guide 340 is perpendicular to its axis (not shown), radiation will be undesirably reflected back from that surface and a portion of this radiation will be collected by the receiving fiber 92. Such "stray light" will interfere with the measurements being made. Likewise, if a window 160 is located at the end of the probe is oriented perpendicular to the probe axis, reflections from it will also contribute to stray light. Where the collecting field of view (angle of acceptance) of the receiving fiber 92 is the same as the transmitting field of view (angle of divergence) of the transmitting fiber (i.e. typically +/−8.4 deg. within the light guide 340), any reflected radiation propagating within this range of angles and falling within the area of the light guide 340 can contribute to stray light.

To eliminate the problem of stray light resulting from reflections at both the target-side refractive surface 346 of the light guide 340, and from the window 160, I have angled the end 346 of the light guide relative to its axis. To eliminate contributions from internal reflection at the target-side surface, it is merely necessary to cock the end surface by an angle $\gamma$ that is greater than $\alpha'$. However, this is not sufficient to eliminate stray light contributions from the first and second refractive surfaces (not separately numbered) of the probe window 160. This can be understood with reference to FIG. 11, an enlargement of the tip region of a probe showing the paths of typical rays travelling between the target-side surface 146, 246, 346 of any one of the light guides 140, 240, 340, and the orthogonal window 160.

On exiting the light guide 340, the transmitted radiation is refracted away from the normal to the exiting surface 346. A ray which was originally parallel to the axis will emerge at an angle of $\beta$ relative to the axis, where $\beta$ is related to the other angles shown by the equations given below. The half angle spread of the output beam will be equal to $\alpha''$ where $\alpha''$ is approximately equal to $\alpha$. It can be shown that we can eliminate stray light contributions from window reflections by ensuring that no exiting rays are perpendicular to the window surfaces. In other words, we require that $\gamma$ is greater than $\alpha''$. We can determine the required light guide end surface angle, $\gamma$, by using the following expressions:

$$\beta = \phi - \phi', \ \phi' = \gamma, \text{ and } \sin \phi = n \sin \phi'. \tag{4}$$

Using these expressions and setting $\gamma = 25$ deg. results in $\beta = 14.3$ deg. this is sufficient to "theoretically" ensure that all of the rays reflected from the window 160 will be outside of the field of view of the collecting fiber. It is only theoretically sufficient because there may be imperfections in the system that cause rays to reflect or refract at other than anticipated angles.

Figure 12:
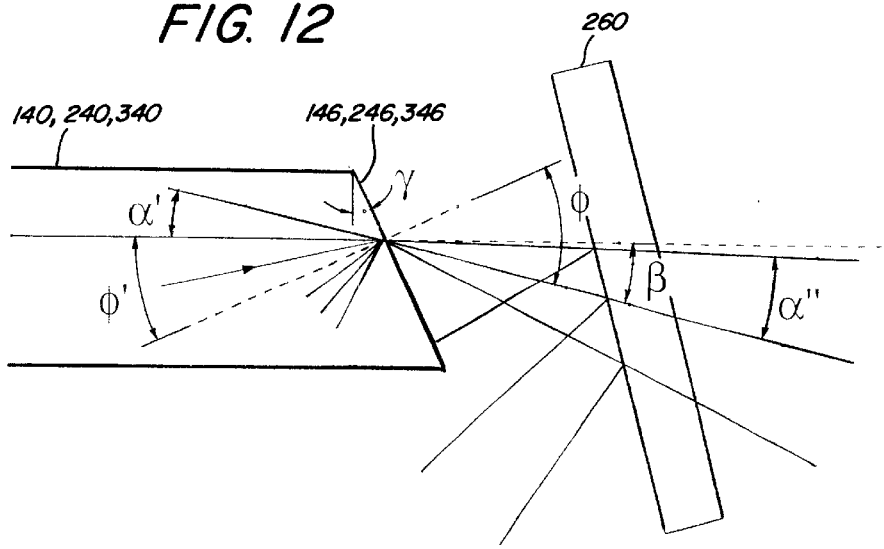
FIG. 12 is a close-up schematic view of a third exemplary fiber coupling structure wherein the axes of the fibers are canted relative to the axis of the solid light guide and wherein the overall fiber bundles is imaged onto the fiber-end of the solid light guide with an intermediate lens.

FIG. 12 presents an embodiment (preferred) that addresses the limitations in the theoretical solution of FIG. 11. In particular, here we not only use a solid light guide 140, 240, 340 with a canted target-side end surface 146, 246, 346, we also use a canted window 260 that optically "cooperates" with the canted target-side end surface 146, 246, 346 to provide further resistance to stray light. This embodiment recognizes the fact that some rays exiting from the light guide 140, 240, 340 will be parallel to the optical axis and makes sure that such refracted-to-parallel rays are incident on the first and second surfaces of the window 260 at an angle so that they are harmlessly reflected back toward the detectors fiber angle of acceptance, rather than reflected back within that angle of acceptance as stray light. The bottom line goal here is to eliminate perpendicular incidence on the window 260.

Although the required surface angles of the fiber-side end surfaces 142, 242 and the target-side end surfaces 146, 246, respectively, are not necessarily the same, it may be appropriate to make them the same, especially when the probe 100, 200 is intended for use over a wide spectral range. This will minimize the effects of dispersion, especially for rays that travel straight through the light guide 140, 240 without being reflected from its axial surface. As shown in FIG. 6, however, it may be desirable to make the target-side end surface 246 more canted than the fiber-side end surface 246 so as to provide some room for error due to imperfections. As shown, the inventor has settled on 15 deg. for the fiber-side end surface 146 and double that angle, or 30 deg., for the target-side end surface 246. The window 260 is preferably canted at an angle between about 15 and 30 degs., the preferred embodiment using 15 deg. as shown in FIG. 6.

FIGS. 13 to 17 are schematic representations of various light guide lengths and various target-end configurations that are encompassed by this invention. As suggested by the "cloud" between the fibers 91, 92 and the fiber-side end surfaces of these embodiments, the target-side of each embodiment may be modified and combined with other structure to form any desired fiber coupling structure including, but not limited to the above-disclose fiber coupling structures 120, 220, 320, 420.

Figure 13:
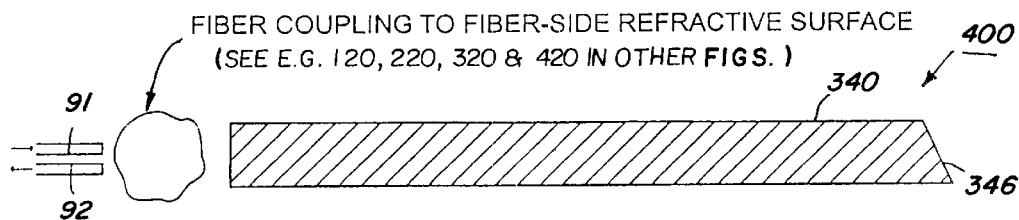

FIG. 13 represents an alternative probe 400 wherein the solid light guide 340 is sufficiently long as to occupy substantially all of the probe body (not shown), that has a target-side end surface 346 that is a flat bevel, and that is exposed to the target at the end of the probe body without use of a window.

Figure 14:
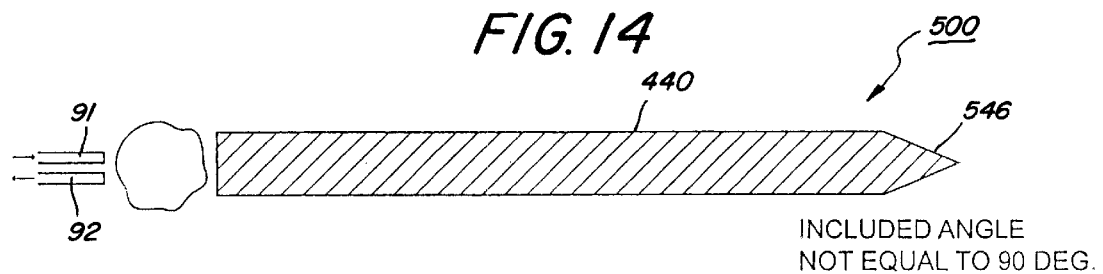

FIG. 14 represents another alternative probe 500 using a solid light guide 540 having a target-side refractive surface 546 consisting of either a rooftop or a cone shape that is either steep (as shown) or shallow (not shown) so as to provide protection from stay light but not form a retroreflector with an included angle of 90 degrees.

Figure 15:
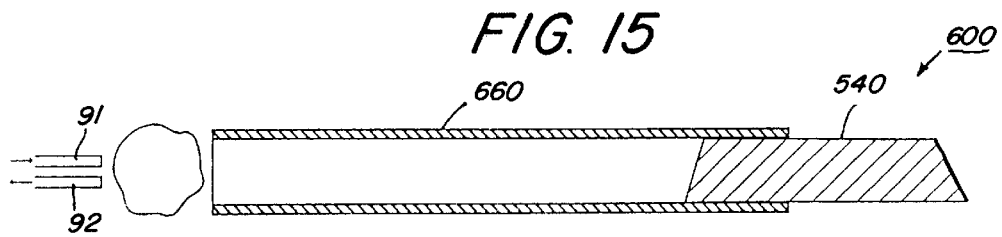

FIG. 15 represents another alternative probe 600 wherein a solid light guide 640 is relatively short and is interfaced to the fibers 91, 92 through a hollow light pipe 660.

Figure 16:
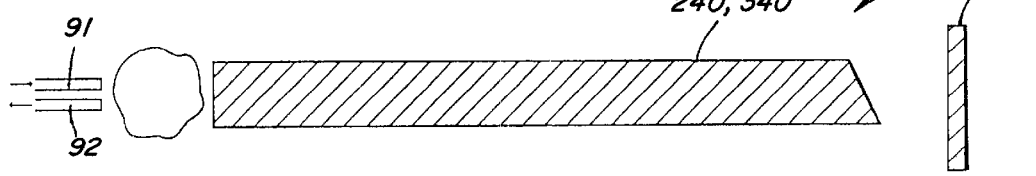
Figure 17:
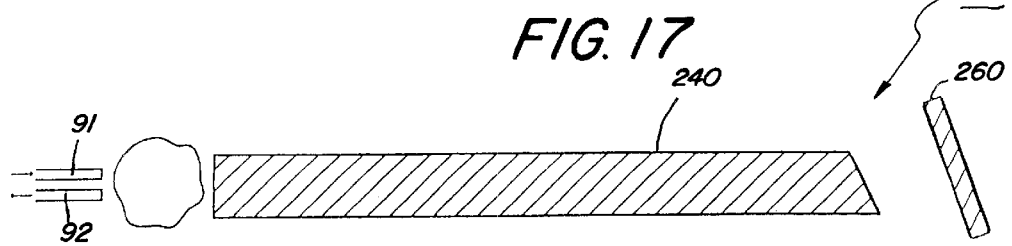

FIG. 16 represents a probe 1000, 300 that includes a structure as shown in FIGS. 2 to 4, or FIG. 7, as discussed above, i.e. wherein a sold light guide 340 is located behind an orthogonal window 160; and FIG. 17 represents a probe 200 that includes a structure as shown in FIGS. 5 to 6, as discussed above, wherein a sold light guide 240 is located behind a canted window 260.

What is claimed is:

1. A diffuse reflectance probe for connection to a illumination fiber for carrying radiation from a remote source and illuminating a target and for connection to a back to a remote detector for diffuse reflectance analysis, the diffuse reflectance probe comprising:

a solid light guide having a fiber end with a fiber-side refractive surface, a target end with a target-side refractive surface, and an optical axis extending between the fiber end and the target end; and a fiber coupling structure optically interfacing the fiber-side refractive surface to the illumination fiber and to the detector fiber;

the target-side refractive surface being oriented relative to the normal of the optical axis to minimize stray radiation that comes from the remote fiber and does not reach the target, but rather is reflected back toward the detector fiber via the solid light guide and the fiber coupling structure, from entering the detector fiber and overpowering the target-modified radiation; and wherein the solid light guide carries both radiation from the source and target-modified radiation.

2. The diffuse reflectance probe of claim 1 wherein the illumination fiber and the detector fiber are contained in a fiber bundle for at least part of their length.

3. The diffuse reflectance probe of claim 2 further comprising a plurality of illumination fibers and a plurality of detector fibers.

4. The diffuse reflectance probe of claim 1 wherein no further refractive surfaces are interposed between the target-side refractive surface and the target.

5. The diffuse reflectance probe of claim 1 further comprising a window interposed between the target-side refractive surface and the target.

6. A diffuse reflectance probe for connection to a illumination fiber for carrying radiation from a remote source and illuminating a target and for connection to a return fiber for carrying target-modified radiation that is diffusely reflected from the target back to a remote detector for diffuse reflectance analysis, the diffuse reflectance probe comprising:

a solid light guide having a fiber end with a fiber-side refractive surface, a target end with a target-side refractive surface, and an optical axis extending between the fiber end and the target end; and a fiber coupling structure optically interfacing the fiber-side refractive surface to the illumination fiber and to the detector fiber;

the target-side refractive surface being oriented relative to the normal of the optical axis to minimize stray radiation that comes from the remote fiber and does not reach the target, but rather is reflected back toward the detector fiber via the solid light guide and the fiber coupling structure, from entering the detector fiber and overpowering the target-modified radiation;

a window interposed between the target-side refractive surface and the target;

wherein the window has first and second refractive window surfaces that potentially contribute to stray radiation by reflecting some radiation from the illumination fiber back toward the detector fiber via the solid light guide and the fiber coupling structure; and wherein the acute angle of the target-side refractive surface at the target end of the solid light guide is oriented relative to the normal of the optical axis and to the first and second refractive window surfaces as to also cause substantially all radiation that is reflected from the first and second refractive window surfaces to reach the detector fiber at angles that are outside the detector fiber's half angle of acceptance.

7. The diffuse reflectance probe of claim 6 wherein the first and second refractive window surfaces are substantially parallel to one another.

8. The diffuse reflectance probe of claim 7 wherein the first and second refractive window surfaces are oriented substantially perpendicularly to the optical axis.

9. The diffuse reflectance probe of claim 7 wherein the first and second refractive window surfaces are oriented at an acute angle to normal to the optical axis.

10. The diffuse reflectance probe of claim 7 wherein the first and second window surfaces are oriented at an acute angle relative to the normal of the optical axis to further ensure that illumination rays within the light guide that are directed outside of the angle of divergence that is mathematically expected, due to imperfections and the like, are still reflected from the first and second window surfaces at an angle that causes such rays to be refracted through the second refractive surface at the target end of the light guide at an angle that is outside the detector fiber's half angle of acceptance.

11. The diffuse reflectance probe of claim 1 wherein the target-side refractive surface is a flat beveled surface oriented at an acute angle relative to the normal of the optical axis.

12. A diffuse reflectance probe for connection to a illumination fiber for carrying radiation from a remote source and illuminating a target and for connection to a return fiber for carrying target-modified radiation that is diffusely reflected from the target back to a remote detector for diffuse reflectance analysis, the diffuse reflectance probe comprising:

a solid light guide having a fiber end with a fiber-side refractive surface, a target end with a target-side refractive surface, and an optical axis extending between the fiber end and the target end; and a fiber coupling structure optically interfacing the fiber-side refractive surface to the illumination fiber and to the detector fiber;

the target-side refractive surface being oriented relative to the normal of the optical axis to minimize stray radiation that comes from the remote fiber and does not reach the target, but rather is reflected back toward the detector fiber via the solid light guide and the fiber coupling structure, from entering the detector fiber and overpowering the target-modified radiation;

wherein the target-side refractive surface is a flat beveled surface oriented at an acute angle relative to the normal of the optical axis;

wherein the illumination fiber has a numerical aperture that provides a limited field of coverage defined by a half angle of divergence;

wherein the detector fiber has a numerical aperture that provides a limited field of view defined by a half angle of acceptance; and wherein the acute angle of the target-side refractive surface is sufficiently large as to cause substantially all radiation that exits the illumination fiber at angles within the half angle of divergence, is refracted first by the fiber-side refractive surface and is then internally reflected by the target-side refractive surface, to be internally reflected back to the fiber end of the solid light guide and then refracted by the fiber-side refractive surface to angles that are outside the detector fiber's half angle of acceptance.

13. The diffuse reflectance probe of claim 12 wherein the numerical apertures of the source and detector fibers are substantially equal such that the illumination fiber's half angle of divergence is substantially equal to the detector fiber's half angle of acceptance.

14. The diffuse reflectance probe of claim 13 wherein the acute angle is at least as great as an angle that results in a most divergent illumination ray being reflected and thereafter approaching the detector fiber at an angle that is greater than a maximum acceptance angle of the detector fiber.

15. The diffuse reflectance probe of claim 12 wherein the numerical apertures of the source and detector fibers are different such that the illumination fiber's half angle of divergence is different than the detector fiber's half angle of acceptance.

16. The diffuse reflectance probe of claim 15 wherein the acute angle is at least as great as an angle that results in a most divergent illumination ray being reflected and thereafter approaching the detector fiber at an angle that is greater than a maximum acceptance angle of the detector fiber.

17. A diffuse reflectance probe for connection to a illumination fiber for carrying radiation from a remote source and illuminating a target and for connection to a return fiber for carrying target-modified radiation that is diffusely reflected from the target back to a remote detector for diffuse reflectance analysis, the diffuse reflectance probe comprising:

a solid light guide having a fiber end with a fiber-side refractive surface, a target end with a target-side refractive surface, and an optical axis extending between the fiber end and the target end; and a fiber coupling structure optically interfacing the fiber-side refractive surface to the illumination fiber and to the detector fiber;

the target-side refractive surface being oriented relative to the normal of the optical axis to minimize stray radiation that comes from the remote fiber and does not reach the target, but rather is reflected back toward the detector fiber via the solid light guide and the fiber coupling structure, from entering the detector fiber and overpowering the target-modified radiation; and wherein the fiber coupling structure is detachable from the source and detector fibers.

18. A diffuse reflectance probe for connection to a illumination fiber for carrying radiation from a remote source and illuminating a target and for connection to a return fiber for carrying target-modified radiation that is diffusely reflected from the target back to a remote detector for diffuse reflectance analysis, the diffuse reflectance probe comprising:

a solid light guide having a fiber end with a fiber-side refractive surface, a target end with a target-side refractive surface, and an optical axis extending between the fiber end and the target end; and a fiber coupling structure optically interfacing the fiber-side refractive surface to the illumination fiber and to the detector fiber;

the target-side refractive surface being oriented relative to the normal of the optical axis to minimize stray radiation that comes from the remote fiber and does not reach the target, but rather is reflected back toward the detector fiber via the solid light guide and the fiber coupling structure, from entering the detector fiber and overpowering the target-modified radiation; and wherein the illumination fiber has a numerical aperture that provides a field of coverage defined by a half angle of divergence, wherein radiation from the illumination fiber travels through a first medium having a first index of refraction before entering the fiber-side refractive surface of the solid light guide, and wherein the solid light guide is made from a second medium having a second greater index of refraction such that the radiation travels through the solid light guide at a reduced half angle of divergence.

* * * * *